United States Patent
Benderly

(10) Patent No.: US 7,576,030 B2
(45) Date of Patent: Aug. 18, 2009

(54) ACTIVATED IGNITION PROMOTERS FOR METAL CATALYZED REACTIONS

(75) Inventor: Abraham Benderly, Elkins Park, PA (US)

(73) Assignee: Rohm and Haas Company, Philadelphia, PA (US)

( * ) Notice: Subject to any disclaimer, the term of this patent is extended or adjusted under 35 U.S.C. 154(b) by 383 days.

(21) Appl. No.: 11/143,046

(22) Filed: Jun. 2, 2005

(65) Prior Publication Data

US 2005/0271572 A1    Dec. 8, 2005

Related U.S. Application Data

(60) Provisional application No. 60/576,447, filed on Jun. 3, 2004.

(51) Int. Cl.
| | | |
|---|---|---|
| *B01J 23/10* | (2006.01) | |
| *B01J 23/36* | (2006.01) | |
| *B01J 23/42* | (2006.01) | |
| *B01J 23/44* | (2006.01) | |
| *B01J 23/46* | (2006.01) | |
| *B01J 23/50* | (2006.01) | |
| *B01J 23/52* | (2006.01) | |

(52) U.S. Cl. .................... 502/304; 502/300; 502/325; 502/326; 502/330; 502/331; 502/337; 502/339; 502/344; 502/345; 502/439

(58) Field of Classification Search .............. 423/390.1, 423/392; 502/325, 339, 300, 304, 326, 330, 502/331, 337, 344, 345, 439
See application file for complete search history.

(56) References Cited

U.S. PATENT DOCUMENTS

| | | | | |
|---|---|---|---|---|
| 3,470,019 | A | | 9/1969 | Steele |
| 3,900,646 | A | * | 8/1975 | Clyde .......................... 427/595 |
| 3,998,758 | A | * | 12/1976 | Clyde .......................... 502/307 |
| 4,863,893 | A | | 9/1989 | Farrauto et al. |
| 5,242,882 | A | * | 9/1993 | Campbell .................... 502/325 |
| 5,356,003 | A | | 10/1994 | Gretz et al. |
| 5,401,483 | A | * | 3/1995 | Ostroff ........................ 423/376 |
| 5,690,900 | A | * | 11/1997 | Smojver ...................... 423/392 |
| 6,649,134 | B2 | * | 11/2003 | Gorywoda et al. ......... 423/239.1 |
| 6,743,404 | B1 | * | 6/2004 | Schumacher et al. ...... 423/239.1 |
| 7,192,566 | B2 | * | 3/2007 | Duclos et al. ............... 423/351 |

FOREIGN PATENT DOCUMENTS

GB           461127          2/1937

* cited by examiner

*Primary Examiner*—Wayne Langel
(74) *Attorney, Agent, or Firm*—Marcella M. Bodner; Stephen E. Johnson

(57) ABSTRACT

The inventors have discovered catalyst ignition promoters comprising one or more activated metals. The catalyst ignition promoters are easily prepared from a number of metal sources, including spent catalysts, are activated quickly and provide effective catalyst ignition independent of the quality of the metals that comprise the catalytic converter. The one or more activated metals comprising the ignition promoter are prepared by contacting them with one or more chemical treatments. The activated metal components are prepared into suitable articles, referred to as ignition strips, that are placed in contact with one or more oxidative coupling catalysts, typically in the form of gauzes. The ignition promoters reduce the activation energy for catalyst ignition (also referred to "light off"), enabling ignition of catalyst gauzes that are new, used, contaminated, damaged and combinations thereof at a relatively low auto-ignition temperatures.

2 Claims, No Drawings

ACTIVATED IGNITION PROMOTERS FOR METAL CATALYZED REACTIONS

CROSS REFERENCE TO RELATED PATENT APPLICATIONS

This is a non-provisional patent application of co-pending U.S. provisional patent application Ser. No. 60/576,447 filed Jun. 3, 2004.

The present invention relates to promoting ignition of catalysts used in metal catalyzed reactions. In particular, the invention is directed to ignition promoting articles used in industrial scale metal catalyzed oxidation reactions including, but not limited to, the manufacture of hydrogen cyanide (Andrussov process), nitric acid (Ostwald process), synthesis gas (carbon monoxide and hydrogen), olefins, alkynes and formaldehyde. The invented ignition promoting articles improves catalytic converter light off efficiency, provides lowered temperatures for catalyst light off, provides light off of used, damaged and or contaminated catalysts, prevents multiple light off failures and increases the overall yields of products at constant reactant(s) conversion from a particular catalyst. The invention is further directed to methods for preparing activated metal ignition promoters and to metal catalyzed processes using the catalyst ignition promoters.

A number of important chemical manufacturing processes are metal catalyzed oxidations. Examples include, but are not limited to, manufacture of hydrogen cyanide from methane and ammonia, acetylene from methane and oxygen, nitric acid from the oxidation of ammonia (Ostwald process), synthesis gas from steam reforming of methane, ethylene from ethane, propylene from propane, and formaldehyde from methanol. The commercial manufacture of hydrogen cyanide is a metal catalyzed oxidative coupling of methane and ammonia. Ignition of reactants occurs by passing preheated feed gases on platinum/rhodium gauzes at temperatures greater than 270° C. Unfortunately, ignition start up problems, including failures to ignite new catalysts, used catalysts, contaminated catalysts and damaged catalysts results in significant production losses, including additional catalyst costs and reactor down time associated with subsequent failed attempts to restart catalyst ignition. In addition, overall yields of catalyzed products are negatively impacted as a result of one or more catalyst ignition failures. There are a number of possible causes for catalyst ignition failure including, but not limited to, contamination of the catalyst due to one or more organic residues from feed gases, one or more lubricating and/or compressor oils associated with the reactor and combinations thereof. Despite techniques known in the art to enhance the catalyzed ignition process, including increasing the flammability of the incoming reactant(s) feed, raising feed temperature, and increasing reactor pressure, catalyst ignition problems have provided a number of obstacles to overcome.

Catalyst ignition (also referred to as catalyst light off) at relatively low temperature is highly desirable. U.S. Pat. No. 4,863,893 describes one approach to lowering the ignition temperature of ammonia oxidation in the manufacture of nitric acid, which involves use of platinum-rhodium and platinum-palladium-rhodium gauzes bearing a platinum coating in excess of 4.0 g/m² of platinum loading to the bulk area of the gauze (considered a sheet) to lower the ignition temperature required for light off in ammonia oxidation, especially if hydrogen is used as ignition fuel. Unfortunately, plating large or entire areas of woven catalyst gauzes with platinum black is expensive, cumbersome and not commercially feasible. It would be highly desirable, therefore, to provide one or more catalyst ignition promoters which can initiate catalyst ignition at relatively low auto-ignition temperatures. One impediment to a commercially viable catalyst ignition promotion process is the identification of one or more optimal ignition promoters that provide adequate catalyst ignition, including catalyst ignition in the presence of one or more contaminants, ignition of used catalysts, ignition of damaged catalysts, catalyst ignition coupled to good product(s) conversion at constant reactant(s) conversion, including suitable product selectivity. Despite attempts to provide new and improved catalysts for metal catalyzed oxidations, no attempts have been made to identify catalyst ignition promoters or that utilize activated metals as igniter strips for catalyst ignition.

The inventors have discovered catalyst ignition promoters comprising one or more activated metals that are easily prepared from a number of metal sources, including spent catalysts, new catalysts, damaged catalysts, contaminated catalysts and combinations thereof. The metals are activated quickly and are prepared in the form of ignition promoting articles that are placed in contact with the catalysts to provide effective catalyst ignition, independent of the quality of the metals that comprise the catalytic converter. The one or more activated metals comprising the ignition promoter are prepared by contacting them with one or more chemical treatments or combinations of one or more chemical and physical treatments. The activated metal components are fabricated into suitable ignition promoting articles, referred to as ignition strips, that are placed in contact with one or more catalysts. The ignition promoters reduce the activation energy for catalyst ignition (also referred to "light off"), enabling ignition of catalyst gauzes that are new, used, contaminated, damaged and combinations thereof at a relatively low auto-ignition temperatures.

Accordingly, there is provided a catalyst ignition promoting article comprising: one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, the article further comprising less than 1 percent by weight of a metal coating, based on the weight of the article, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, wherein the metal is deposited on the article using one or more chemical treatments or a combination of one or more chemical and physical treatments.

There is provided a process for preparing one or more catalyst ignition promoters comprising the step of treating one or more sections of a catalyst comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, with one or more chemical treatments or a combination of one or more chemical and physical treatments; wherein each section of the catalyst is coated with a metal coating comprising less than 1 percent by weight of a metal coating, based on the weight of the catalyst, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

There is provided a process for preparing one or more catalyst ignition promoting articles comprising the steps of: (a) preparing one or more articles from one or more sections of a catalyst comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof; (b) contacting each article with one or more chemical treatments or a combination of one or more chemical and physical treatments, wherein each article is coated with a metal coating comprising less than 1 percent by weight of a metal coating, based on the weight of the article, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

There is provided a process for lowering the ignition temperature of one or more reactants using one or more metal catalysts comprising the step of contacting each catalyst with one or more ignition promoting articles.

There is provided a process for igniting one or more catalysts selected from the group consisting of new catalysts, used catalysts, recycled catalysts, reconditioned catalysts, damaged catalysts, contaminated catalysts and combinations thereof, comprising the step of contacting each catalyst with one or more ignition promoting articles.

There is provided a process for reconstructing catalytic sites in a catalyst comprising the step of contacting the catalyst with one or more ignition promoting articles or treating one or more sections of a catalyst comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, with one or more chemical treatments or a combination of one or more chemical and physical treatments; wherein each section of the catalyst is coated with a metal coating comprising less than 1 percent by weight of a metal coating, based on the weight of the catalyst, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

There is provided a process for increasing catalytic sites in a catalyst comprising the step of contacting the catalyst with one or more ignition promoting articles or treating one or more sections of a catalyst comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, with one or more chemical treatments or a combination of one or more chemical and physical treatments; wherein each section of the catalyst is coated with a metal coating comprising less than 1 percent by weight of a metal coating, based on the weight of the catalyst, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

There is provided a process for manufacturing hydrogen cyanide comprising the step of contacting a platinum/rhodium catalyst with one or more ignition promoting articles.

Accordingly, the present invention provides one or more catalyst ignition promoting articles for industrial scale metal catalyzed reactions. The catalyst ignition promoting articles are easily prepared from a number of metal sources, including but not limited to for example, metals used to prepare catalysts, new catalysts, spent catalysts, damaged catalysts, recycled catalysts, reconditioned catalysts, contaminated catalysts and combinations thereof. According to one embodiment, a specific ignition promoting article is prepared from its corresponding catalyst as the metal source. According to a separate embodiment, the specific ignition promoting article is prepared from metal sources other than the corresponding catalyst. The ignition promoters reduce the activation energy for catalyst ignition (also referred to "light off"), enabling ignition of catalyst gauzes that are new, used, contaminated, damaged, recycled, reconditioned and combinations thereof at a relatively low auto-ignition temperatures.

Suitable metals and metal sources used in accordance with the invention include, but are not limited to, nickel, platinum, palladium, cobalt, rhodium, silver, gold, copper, iridium, rhenium, ruthenium, molybdenum, vanadium, niobium, indium, cerium and alloys thereof. Suitable alloys include, but are not limited to for example, binary alloys such as Pt/Rh, Pt/Ni, Pt/Co, Pt/Ag, Pt/Au, Pt/Cu, Pt/Ir, Pt/Re, Pt/Ru, Pt/Mo, Pt/Ce, Pd/Rh, Pd/Ni, Pd/Co, Pd/Ag, Pd/Cu, Rh/Co, Rh/Ni, Rh/Ag, Rh/Ru; ternary alloys such as Pt/Pd/Rh, Pt/Pd/Ni, Pt/Pd/Ag, Pt/Pd/Ru, and Pt/Pd/Co. Other suitable metals include intermetallics selected from the group consisting of nickel, platinum, palladium, cobalt, rhodium, silver, gold, copper, iridium, rhenium, ruthenium, molybdenum, and cerium. Examples include, but are not limited to, $Pt_{0.1-1.99}Rh_{0.99-0.01}$, $Pt_2Rh$, $Ni_{0.1-1.99}Pt_{0.99-0.01}$, $Pt_xRh_y$, $Pt_xNi_y$, $Pt_xCo_y$, $Pt_xRh_yIr_z$, and $Pt_xRh_yIr_z$, wherein x=0.1-100, y=0.1-100 and z=0.1-100. As used herein, intermetallics refer to discrete intermediate compounds having stoichiometric or non-stoichiometric formulas, as compared to alloys (solid solutions of two or more metals).

The ignition promoting article is prepared in a variety of three-dimensional forms. According to one embodiment, the three-dimensional form of a specific ignition promoting article corresponds to the three-dimensional form of a specific catalyst. According to a separate embodiment, the three-dimensional form of a specific ignition promoting article corresponds to a three-dimensional form different than a specific catalyst. Suitable forms of the ignition promoting article include, but are not limited to for example, fibers, wires, needles, foams, spongy masses, porous solids, porous particles, fibrous sheets, knitted gauzes, woven gauzes and combinations thereof. According to one embodiment, the ignition promoting articles takes the form of the catalyst used in a specific metal catalyzed reaction. According to a separate embodiment, the ignition promoting articles takes a form different from the catalyst used in a specific metal catalyzed reaction.

The ignition promoting article further comprises less than 1 percent by weight of a metal coating, based on the weight of the article. According to one embodiment, the weight of the metal coating, based on the weight of the article is between 0.01 and 1 percent be weight, including from 0.05 to 0.75 percent by weight. The metal coating comprises one or more metals selected from the group consisting of nickel, platinum, palladium, cobalt, rhodium, silver, gold, copper, iridium, rhenium, ruthenium, molybdenum, vanadium, niobium, indium, cerium, alloys thereof, binary alloys thereof, ternary alloys thereof, intermetallics thereof, and combinations thereof, wherein the metal is deposited on the article using one or more chemical treatments or a combination of one or more chemical and physical treatments. According to one embodiment the metal coating comprises the same composition as the catalyst. According to separate embodiment, the metal coating comprises a different composition as the catalyst.

The amount of metal loading on the ignition promoting article is less than 0.5 g/m² of metal(s) per square meter of ignition promoting article. According to one embodiment the amount of metal loading is between 0.0003 g/cm² to 0.5 g/m², including from 0.004 g/cm² to 0.001 g/m².

The process for preparing one or more catalyst ignition promoting articles comprises the steps of: (a) preparing one or more articles from one or more sections of a catalyst comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof: (b) contacting each article with one or more chemical treatments or a combination of one or more chemical and physical treatments, wherein each article is coated with a metal coating comprising less than 1 percent by weight of a metal coating, based on the weight of the article, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

Activated metal is deposited on the ignition promoting article or sections of the catalyst using one or more chemical treatments or a combination of one or more chemical and physical treatments. As used herein, activated metals refer to metals having a higher amount and proportion of catalytically active sites as compared to untreated metals. According to one embodiment of the invention, the activated metal components are prepared into ignition promoting articles, also referred to as ignition strips, that are placed in contact with a specific catalyst. According to a separate embodiment, activated metal components are incorporated in the treated sections of the catalyst. One advantage of the invention is that the ignition promoters in the form of small strips or treated sections of the catalyst have a large total surface area, as compared to completely coated, large area catalytic gauzes characterized by surface coatings in excess of 50 cm²/g to 500 cm²/g of metal required for ignition. A second advantage is that the metal loading in the ignition promoters of the present invention is small as to compared to conventional methods requiring at least 0.5 g metal/m² catalyst for ignition. A third advantage of the invention is that the catalyst ignition promoting articles are quickly prepared and contacted with the catalyst, minimizing reactor down time as compared to special operations required for coating large area catalysts, storing the coated catalysts safely and corresponding costs associated with the relatively large amounts of platinum coating required. A fourth advantage of the invention is that used catalysts, damaged catalysts, contaminated catalyst and combinations thereof are successfully ignited using the ignition promoting articles.

One or more chemical treatments or combinations of one or more chemical and physical treatments are used to incorporate activated metals in the ignition promoters so that they contain higher amounts and proportions of catalytically active sites as compared to untreated metals. Suitable chemical treatments and physical treatments include, but are not limited to for example, contacting ignition promoting strip with one or more metal compounds. The one or more metal compounds are thermally and photochemically decomposed, including chemically and electrochemically reduced, to provide active catalytic metal sites on the ignition promoting strips. Other methods of incorporating activated metals on the ignition promoting strips include, but are not limited to for example, chemical vapor deposition of catalytically active metals on the surface of the ignition strip, precipitation of catalytically active metals on the surface of the ignition strip using electroless deposition, electroplating catalytically active metals on the surface of the ignition strip, sputtering catalytically active metals on the surface of the ignition strip, and physical vapor deposition of catalytically active metals on the surface of the ignition strip.

Suitable metal compounds used to deposit activated metals on ignition promoting strips include, but are not limited to for example, contacting the ignition promoting article with metal compounds selected from the group consisting of platinum black, Raney Ni, metal halides wherein the metal includes, but is not limited to for example, nickel, platinum, palladium, cobalt, rhodium, silver, gold, copper, iridium, rhenium, ruthenium, molybdenum, vanadium, niobium, indium, cerium and combinations thereof and wherein the halides are selected from the group consisting of F, Cl, Br, I and combinations thereof, metal ammonia complexes, organometallic compounds, including but not limited to for example, metal carbonyls and metal olefins wherein the metal includes, but is not limited to for example, nickel, platinum, palladium, cobalt, rhodium, silver, gold, copper, iridium, rhenium, ruthenium, molybdenum, vanadium, niobium, indium, cerium and combinations thereof, and metal hydride complexes.

There is provided a process for igniting one or more catalysts selected from the group consisting of new catalysts, used catalysts, recycled catalysts, reconditioned catalysts, damaged catalysts, contaminated catalysts and combinations thereof, comprising the step of contacting each catalyst with one or more ignition promoting articles.

According to one embodiment, ignition promoting articles of the invention reduce the activation energy for light off of a new catalyst, enabling the new catalyst to ignite at relatively lower temperatures, namely temperatures similar to that of corresponding used catalysts which have relatively higher surface areas. Ignition of reactants occurs at the sites where the ignition promoting articles contact the catalyst, subsequently leading to complete ignition of the catalyst, as confirmed by visual observations and by temperature measurements using thermocouple devices.

According to a separate embodiment, ignition promoting articles of the invention afford light off of catalysts contaminated with one or more organic compounds that include, but are not limited to for example, lubricating oils, compressor oils, paraffin residues, $C_8$-$C_{22}$ hydrocarbons in reactants, oil residues, residues in reactants, reactor debris, soot, dust, product residues and combinations thereof. Ignition of reactants occurs at uncontaminated sites where the ignition promoting articles contact the catalyst, subsequently leading to complete ignition of the catalyst, as confirmed by visual observations and by temperature measurements using thermocouple devices. Ignition promoted light off is successful in contaminated catalysts using a short pre-heating period while admitting the feed into the catalytic converter for immediate light off. One advantage is that this method minimizes further contamination of the catalyst, as compared to conventional light off methods.

According to a separate embodiment, ignition promoting articles of the invention afford light off of catalysts damaged by events that that include, but are not limited to for example, high temperature flare off of reactants, oxidation of catalyst, destruction of catalytic sites, unfavorable reactions not leading to products and combinations thereof. Ignition promoting articles are used contact the catalyst at damaged sites, providing an additional advantage of repair of the damaged catalyst site. Ignition of reactants occurs at damaged sites where the ignition promoting articles contact the catalyst, subsequently leading to complete ignition of the catalyst, as confirmed by visual observations and by temperature measurements using thermocouple devices.

According to a separate embodiment, ignition promoting articles of the invention afford light off of used catalysts, recycled catalysts and reconditioned catalysts by reconstructing catalytic sites. Generation of product specific catalytic sites is a dynamic process during catalysis and catalytic sites are continuously created and destroyed. In some cases, destruction of catalytic sites is so severe that product yields drop precipitously and the reaction is shut down. Ignition promoting articles are successfully used to reconstruct catalytic sites with immediate light off of the used, recycled or reconditioned catalyst. Ignition of reactants occurs at reconstructed catalytic sites where the ignition promoting articles contact the catalyst, subsequently leading to complete ignition of the catalyst, as confirmed by visual observations and by temperature measurements using thermocouple devices.

The present invention provides one or more catalyst ignition promoting articles for industrial scale metal catalyzed reactions.

According to one embodiment, the invention provides activated ignition promoting articles for the production of hydrogen cyanide from the oxidative coupling of methane and ammonia using Pt/Rh gauzes. Such gauzes typically consist of metal alloys, including but not limited to for example, Pt/Rh (90%/10%), Pt/Rh (95%/5%) and Pt/Rh/Pd (90%/5%/5%). Gauzes are typically flat woven meshes of metal wires having a minimum diameter of approximately 0.003 inch (0.008 cm) with at least 80 meshes per inch (31.5 meshes/cm). Ignition promoting articles are prepared by cutting 7-10 irregular or regular sized sections of a used catalyst gauze having a minimum area of 4 cm$^2$. The gauzes were placed in an aqueous solution of a platinum compound and were calcined to decompose the platinum compound to a coating of Pt metal on each gauze. The metal loading on each article ranged from 0.01 to 1% by weight Pt, based on the weight of the article. The articles were placed in contact with Pt/Rh catalyst and ignition temperatures were measured by thermocouple devices. Ignition of preheated feed gases occurred in the vicinity of the ignition promoting articles at temperatures between 230 to 260° C. and climbed to operating temperatures between 1100 and 1250° C. in a plant operating at an optimized reactant mass throughput. Ignition on first attempt occurred with a frequency greater than 95%. The catalytic activation of hydrogen cyanide occurs at crystalline cyanide sites on the surface of the multi-layered gauze.

Suitable compounds used to chemically treat and to incorporate activated metals in ignition promoting strips include, but are not limited to for example, compounds selected from the group consisting of platinum black, platinum sponge Raney Ni, platinum (II) halides ($PtF_2$, $PtCl_2$, $PtBr_2$ and $PtI_2$), platinum (IV) halides ($PtF_4$, $PtCl_4$, $PtBr_4$ and $PtI_4$), platinum (VI) halides ($PtF_6^{2-}$, $PtCl_6^{2-}$, $PtBr_6^{2-}$ and $PtI_6^{2-}$), Zeise salts, ammonia complexes of Pt(II), Pt(IV) and Pt(VI), chloroplatinic acid ($H_2PtCl_6$), bromoplatinic acid ($H_2PtBr_6$), organometallic Pt(0) compounds including but not limited to for example, bis(ethylene)platinum compounds and divinyltetralkylsiloxane Pt(0) compounds, platinum acetylacetonate, platinum cyanide, and platinum hydride complexes. A catalytic form of platinum, platinum black is deposited on the ignition strips by thermal, photochemical decomposition of the platinum compounds listed above. Electrochemical and chemical reduction of platinum compounds also generates platinum black on the ignition strips. Platinum as well as other catalytic metals (e.g. Raney Ni) is also deposited on the ignition strips by chemical or combinations of chemical and physical treatments.

Generation of specific hydrogen cyanide catalytic sites is a dynamic process, with catalytic sites being continuously created and destroyed as the reaction proceeds. During the catalytic process, the surface area of the catalytic gauze increases considerably, restructuring to form facets, pits, whiskers and crystalline catalytic sites and amorphous regions which are catalytically inactive. The restructuring of catalytic sites in the gauze is anisotropic in nature and the crystalline catalytically active sites migrate to amorphous catalytically inactive sites. Towards the end of the lifetime of the gauze, the reaction sites reach the lower metal layers and the aged gauze stops generating new catalytic cyanide sites. Moreover, the population of catalytic sites is gradually reduced over the lifetime of the catalyst, which results in reduced yields of hydrogen cyanide and the catalytic gauze is replaced.

The ignition promoters reduce the activation energy for catalyst ignition (also referred to "light off"), enabling ignition of catalyst gauzes that are new, used, contaminated, damaged and combinations thereof at a relatively low autoignition temperatures. The catalytic ignition promoters of the invention restores hydrogen cyanide catalytic sites to crystalline active forms. The ignition promoters, moreover, enhance the activity of a spent catalyst, resulting in a net increase in the catalytic cyanide sites. The use of activated catalyst ignition promoters has resulted in an unexpected improvement in the reliability of catalyst light off in the manufacture of hydrogen cyanide from methane and ammonia, resulting in higher manufacturing production, reduction of ammonia and methane flaring which damages and or destroys the catalyst and increased catalyst lifetime.

According to a separate embodiment, the invention provides activated ignition promoting articles for the metal catalyzed production of nitric acid from the oxidation of an ammonia-air mixture. Gauzes typically used for the production of nitric acid typically consist of platinum group metal alloys primarily 90% Pt:10% Rh and 90% Pt:5% Rh:5% Pd and are typically woven meshes of about 0.003 of an inch diameter wires at about 80 wires per lineal inch. Other combinations of mesh and wire diameter may be used to advantage. For a detailed report, see Roberts and Gillespie, "Estimation of Platinum Catalyst Requirement for Ammonia Oxidation" 45 Advances in Chemistry Series No. 133, Chemical Reaction Engineering II page 600-611. See also U.S. Pat. No. 3,660,024. Ignition promoting articles are prepared by cutting 7-10 irregular or regular sized sections of a used catalysts gauze having a minimum area of 4 cm$^2$. The gauzes were placed in an aqueous solution of a platinum compound and were calcined to decompose the platinum compound to a coating of Pt metal on each gauze. The metal loading on each article ranged from 0.01 to 1% by weight Pt, based on the weight of the article. The articles were placed in contact with Pt/Rh catalyst and ignition temperatures were measured by thermocouple devices. Ignition of preheated feed gases occurred in the vicinity of the ignition promoting articles at temperatures between 230 to 260° C. in a plant operating at a reactant mass throughput of 8500 lbs/ft$^2$-hr. Ignition on first attempt occurred with a frequency greater than 90%.

Activated ignition promoting articles are prepared from sections of the gauzes as described above and treated with chloroplatinic acid followed by thermal reduction to generate a high concentration of platinum black sites on the ignition strips as compared to the catalytic gauze. The ignition promoting articles of the invention have a number of advantages over completely coating conventional ammonia oxidation catalyst gauzes. One advantage is that the metal loading in the ignition promoters of the present invention is less than the 0.5 g metal/m$^2$ catalyst gauze required for ignition. A second advantage of the invention is that the catalyst ignition promoting articles are quickly prepared and contacted with the catalyst, minimizing reactor down time as compared to special operations required for coating large area catalysts, storing the coated catalysts safely and the expense associated with platinum coating required. A third advantage of the invention is that used catalysts, damaged catalysts, contaminated catalyst and combinations thereof are successfully ignited using the ignition promoting articles.

According to a separate embodiment, the invention provides activated ignition promoting articles for the metal catalyzed production of acetylene from the oxidation of a methane-air mixture. Conventional ignition of reactants occurs by passing preheated feed gases on multiple layers of platinum gauze and Pt-coated monoliths (e.g. α-Alumina) or rhodium gauze at temperatures greater than 500 to 800° C. The catalytic activation of methane and subsequent coupling of methyl radicals occurs at crystalline sites on the surface of the catalyst. Activated ignition strips of the invention are prepared from articles made from the catalysts by depositing a coating of Pt black from platinum compounds described above, Pt/C, combinations of Pt black and Pt/C or by depositing a coating of Rh metal by thermally decomposing rhodium halides (e.g. $RhCl_3$, $(NH_3)_2 RhCl_6$). Ignition promoting articles are prepared by cutting 7-10 irregular or regular sized sections of a used catalyst having a minimum area of 4 cm$^2$. The metal loading on each article ranged from 0.01 to 1% by weight Pt or Rh, based on the weight of the article. The articles were placed in contact with the catalyst and ignition temperatures were measured by thermocouple devices. Ignition of preheated feed gases occurred in the vicinity of the ignition promoting articles at temperatures less than 500° C. operating at space velocities of at least $10^5$ h$^{-1}$.

According to a separate embodiment, the invention provides activated ignition promoting articles for the metal catalyzed production of C2-C8 alkenes from the oxidation of a C2-C8 alkanes-air mixture. Ignition of reactants occurs by passing preheated feed gases on multiple layers of supported and unsupported platinum or rhodium catalysts at temperatures greater than 500° C. Activated ignition strips of the invention are prepared from articles made from the catalysts by depositing a coating of Pt black from platinum compounds described above, Pt/C, combinations of Pt black and Pt/C or by depositing a coating of Rh metal by thermally decomposing rhodium halides (e.g. $RhCl_3$, $(NH_3)_2 RhCl_6$). Ignition promoting articles are prepared by cutting 7-10 irregular or regular sized sections of a used catalyst having a minimum area of 4 cm$^2$. The metal loading on each article ranged from 0.01 to 1% by weight Pt or Rh, based on the weight of the article. The articles were placed in contact with the catalyst and ignition temperatures were measured by thermocouple devices. Ignition of preheated feed gases occurred in the vicinity of the ignition promoting articles at temperatures less than 500° C. operating at space velocities of at least $10^5$ h$^{-1}$.

According to a separate embodiment, the invention provides activated ignition promoting articles for the metal catalyzed production of synthesis gas from the oxidation of methane by steam reforming. Ignition of reactants occurs by passing preheated feed gases on a Ni catalyst, including Ni supported on a ceramic monolith) at temperatures between 1000-1500° C. under pressure (20 bar to 85 bar). Activated ignition strips of the invention are prepared from articles made from the catalysts by depositing a coating of Ni from nickel compounds, including but not limited to for example Raney Ni from an AlNi alloy as described above, or by depositing a coating of Ni metal by chemically reducing or thermally decomposing nickel halides (e.g. $NiCl_2$), nickel carbonyl $Ni(CO)_4$ or organometallic Ni compounds. Ignition promoting articles are prepared by cutting 7-10 irregular or regular sized sections of a used catalyst having a minimum area of 4 cm$^2$. The metal loading on each article ranged from 0.01 to 1% by weight Ni, based on the weight of the article. The articles were placed in contact with the catalyst and ignition temperatures were measured by thermocouple devices. Ignition of preheated feed gases occurred in the vicinity of the ignition promoting articles at temperatures less than 1000° C. operating at space velocities of at least $10^4$ h$^{-1}$.

According to a separate embodiment, the invention provides activated ignition promoting articles for the metal catalyzed production of formaldehyde from the oxidation of methanol using a silver catalyst and wet gas recycle (WGR) or a Pt-coated monolith at short contact times. Ignition of reactants occurs by passing preheated feed gases on crystalline needles of silver at temperatures greater than 600° C. under pressure. The catalytic activation of methane occurs at crystalline $H_2CO$ sites on the surface of the multi-layered gauze. Activated ignition strips of the invention are prepared from articles made from the Ag catalyst by depositing a coating of Ag from silver compounds, including but not limited to for example silver halides (e.g. AgCl, $AgCl_2$—), silver carbonyl Ag(CO) or organometallic Ag compounds. Ignition promoting articles are prepared by cutting 7-10 irregular or regular sized sections of a used catalyst having a minimum area of 4 cm$^2$. The metal loading on each article ranged from 0.01 to 1% by weight Ag, based on the weight of the article. The articles were placed in contact with the catalyst and ignition temperatures were measured by thermocouple devices. Ignition of preheated feed gases occurred in the vicinity of the ignition promoting articles at temperatures less than 600° C. operating at space velocities of at least $10^4$ h$^{-1}$.

The following illustrative examples are provided to further demonstrate the utility of the present invention and are not in any way construed to be limiting. Moreover, the examples provided are representative examples that broadly enable the claimed scope of the invention.

EXAMPLE

Piece of spent or used platinum gauze strips were each cut into irregular sections (2.54 cm by 5.08 cm). The strips were activated by immersing them in an aqueous solution of chloroplatinic acid (13.7%, containing 6.5 wt. % Pt) for 2 hours at room temperature in a crucible. The cloroplatinic acid solution was decanted and the crucible was placed in to a furnace and heated to 450° C. under an argon atmosphere for 2 hours. The gauze strips were cooled to room temperature and stored in the dark under an argon atmosphere. The activated gauze strips incorporated an additional 0.20 wt. % Pt as a result of the chemical treatment. Several pieces of the activated catalyst ignition promoter strip were placed in contact with a platinum catalyst gauze used to manufacture acetone cyanohydrin. Converter light off was successful on the first attempt. Ignition occurred at feed ratios of between 7.0 to 11.5 air/$NH_3$ and between 0.70-1.2 $CH_4$/$NH_3$ as the pressure was increased from between 0 psig to 36 psig. Temperature at ignition was 234° C. and increased to 360° C. (at 28 psig) as measured using a multiplexor temperature recording unit. Thermocouples were placed beneath each igniter strip and it appears that ignition events occurred at each strip before complete gauze ignition occurred within 1 hour, based on the thermocouple readings. The low ignition temperature indicates that the activated strips were unexpectedly effective in promoting complete ignition of the catalytic gauze. Ignition data are summarized in Table 1.

TABLE 1

Data for ignition promoted Pt-gauzes.

| Catalyst Type | Ignition Temp. (° C.) | Ignition attempt |
|---|---|---|
| Pt/Rh gauze (new) | 260 | 1st |
| Pt/Rh gauze (used) | 234 | 1st |
| Pt/Rh gauze (damaged) | 270 | 1st |
| Pt/Rh gauze (new, contaminated) | 273 | 1st |
| Pt/Rh gauze (contaminated) | 230 | 1st |
| Pt/Rh gauze new | 267 | 1st |

The catalyst ignition promoter strips were effective also at igniting damaged and contaminated gauzes, significantly reducing costs associated with ignition failure. In all attempts catalyst light off has been successful on first attempts using the activated ignition promoter strips of the invention.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

What is claimed:

1. A process for preparing one or more catalyst ignition promoters comprising the step of treating one or more sections of a gauze catalyst selected from the group consisting of: a used catalyst, a contaminated catalyst, a damaged catalyst, and combinations thereof, and comprising one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof, with one or more chemical treatments or a combination of one or more chemical and physical treatments; wherein each section of the catalyst is coated with a metal coating comprising between 0.01 and 1 percent by weight of a metal coating, based on the weight of the catalyst, of one or more metals selected from the group consisting of nickel, platinum, palladium, cobalt, rhodium, silver, gold, copper, iridium, rhenium, cerium, alloys thereof, binary alloys thereof, ternary alloys thereof, intermetallics thereof, and combinations thereof.

2. The process according to claim 1, wherein the metal coating is prepared from one or more metal compounds selected from the group consisting of: platinum black, Raney Ni, metal halides (F, Cl, Br, I and combinations thereof), metal ammonia complexes, organometallic compounds, metal carbonyls and metal olefins, metal hydrides and combinations thereof.

* * * * *